(12) United States Patent
Wedekind et al.

(10) Patent No.: US 8,535,708 B2
(45) Date of Patent: Sep. 17, 2013

(54) METHODS FOR INHIBITING A DECLINE IN LEARNING AND/OR MEMORY IN ANIMALS

(75) Inventors: Karen Joy Wedekind, St. Peters, MO (US); Steven Curtis Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 504 days.

(21) Appl. No.: 11/813,119

(22) PCT Filed: Dec. 29, 2005

(86) PCT No.: PCT/US2005/047192
§ 371 (c)(1),
(2), (4) Date: Aug. 18, 2008

(87) PCT Pub. No.: WO2006/071919
PCT Pub. Date: Jul. 6, 2006

(65) Prior Publication Data
US 2009/0004299 A1    Jan. 1, 2009

Related U.S. Application Data

(60) Provisional application No. 60/639,928, filed on Dec. 29, 2004, provisional application No. 60/669,097, filed on Apr. 7, 2005.

(51) Int. Cl.
*A23K 1/17* (2006.01)
*A01N 65/00* (2009.01)

(52) U.S. Cl.
USPC .......................................... 424/442; 424/725

(58) Field of Classification Search
None
See application file for complete search history.

(56) References Cited

U.S. PATENT DOCUMENTS

| | | |
|---|---|---|
| 4,006,266 A | 2/1977 | Bone et al. |
| 4,247,562 A | 1/1981 | Bernotavicz |
| 4,883,672 A | 11/1989 | Shug et al. |
| 5,006,361 A | 4/1991 | Cox |
| 5,030,458 A | 7/1991 | Shug et al. |
| 5,118,505 A | 6/1992 | Koltringer |
| 5,292,538 A | 3/1994 | Paul et al. |
| 5,339,771 A | 8/1994 | Axelrod |
| 5,419,283 A | 5/1995 | Leo |
| 5,569,670 A | 10/1996 | Weischer et al. |
| 5,599,835 A | 2/1997 | Fischer |
| 5,621,117 A | 4/1997 | Bethge et al. |
| 5,728,735 A | 3/1998 | Ulrich et al. |
| 5,730,988 A | 3/1998 | Womack |
| 5,851,573 A | 12/1998 | Lepine et al. |
| 5,883,083 A | 3/1999 | Harless |
| 5,894,029 A | 4/1999 | Brown et al. |
| 5,916,912 A | 6/1999 | Ames et al. |
| 5,937,790 A | 8/1999 | Ito et al. |
| 5,976,568 A | 11/1999 | Riley |
| 5,977,162 A | 11/1999 | Seidman |
| 5,981,767 A | 11/1999 | Tanner et al. |
| 6,080,788 A | 6/2000 | Sole et al. |
| 6,117,477 A | 9/2000 | Paluch |
| 6,190,591 B1 | 2/2001 | van Lengerich |
| 6,232,346 B1 | 5/2001 | Sole et al. |
| 6,335,361 B1 * | 1/2002 | Hamilton ...................... 514/440 |
| 6,365,211 B1 | 4/2002 | Corrigan |
| 6,379,727 B1 | 4/2002 | Addy |
| 6,426,362 B1 | 7/2002 | Miller et al. |
| 6,479,069 B1 | 11/2002 | Hamilton |
| 6,572,888 B2 | 6/2003 | Byrd |
| 6,669,975 B1 | 12/2003 | Abene et al. |
| 6,914,071 B2 | 7/2005 | Zicker et al. |
| 7,282,225 B1 | 10/2007 | Davis et al. |
| 2001/0028896 A1 | 10/2001 | Byrd |
| 2001/0043983 A1 * | 11/2001 | Hamilton ...................... 426/635 |
| 2001/0044448 A1 | 11/2001 | Dib |
| 2002/0006907 A1 | 1/2002 | Gardiner et al. |
| 2002/0076469 A1 * | 6/2002 | Zicker et al. ...................... 426/72 |
| 2002/0076470 A1 * | 6/2002 | Zicker et al. ...................... 426/72 |
| 2002/0115710 A1 * | 8/2002 | Zicker et al. ................... 514/440 |
| 2002/0119182 A1 * | 8/2002 | Zicker et al. ................... 424/442 |
| 2003/0035821 A1 | 2/2003 | Heaton et al. |
| 2003/0044466 A1 | 3/2003 | Markey et al. |
| 2003/0060503 A1 | 3/2003 | Hamilton |
| 2003/0224061 A1 | 12/2003 | Pacioretty et al. |
| 2004/0047896 A1 * | 3/2004 | Malnoe et al. ................. 424/439 |
| 2004/0068010 A1 | 4/2004 | Zicker et al. |
| 2004/0166157 A1 | 8/2004 | Thombre |
| 2005/0100617 A1 | 5/2005 | Malnoe et al. |
| 2005/0123628 A1 | 6/2005 | Zabrecky |
| 2005/0123643 A1 | 6/2005 | Cupp et al. |
| 2008/0317725 A1 | 12/2008 | Baum |
| 2009/0176864 A1 | 7/2009 | Zicker et al. |

FOREIGN PATENT DOCUMENTS

| | | |
|---|---|---|
| CA | 2285490 | 4/2001 |
| CA | 2427692 | 5/2002 |

(Continued)

OTHER PUBLICATIONS

AAFCO, 2003, Official Publication of the American Association of Feed Control Officials, p. 220.

(Continued)

*Primary Examiner* — Brian Gulledge
*Assistant Examiner* — Snigdha Maewall
(74) *Attorney, Agent, or Firm* — Thomas M. Hunter

(57) ABSTRACT

A method for inhibiting a decline in learning and/or memory in an animal comprising maintaining the animal on an antioxidant-fortified diet for a period of at least about 3 years. The diet comprises at least one antioxidant in a total antioxidant amount effective to achieve such inhibition. Suitable antioxidants include vitamin E, vitamin C, α-lipoic acid and antioxidant-containing plant meals. The methods are particularly useful for young adult canines such as dogs.

8 Claims, No Drawings

(56) References Cited

FOREIGN PATENT DOCUMENTS

| | | |
|---|---|---|
| CA | 2427261 | 6/2002 |
| CN | 1323165 A | 11/2001 |
| CN | 1829448 A | 9/2006 |
| CN | 101107012 | 1/2008 |
| DE | 19818563 | 10/1999 |
| EP | 0427247 | 5/1991 |
| EP | 1118332 | 7/2001 |
| EP | 1247456 | 10/2002 |
| EP | 1637041 | 3/2006 |
| EP | 1339292 | 12/2009 |
| JP | H2-49723 A | 2/1990 |
| JP | H10-042798 A | 2/1998 |
| JP | 2003-052338 A | 2/2003 |
| JP | 2003-261456 A | 9/2003 |
| JP | 2003-529347 | 10/2003 |
| JP | 2004-512053 A | 4/2004 |
| JP | 2004-519241 A | 7/2004 |
| JP | 2006-219467 | 8/2006 |
| JP | 2007-062326 | 3/2007 |
| JP | 2007-062332 | 3/2007 |
| JP | 2007-308468 | 11/2007 |
| JP | 2008-063234 | 3/2008 |
| JP | 2008-280322 A | 11/2008 |
| RU | 2071319 | 1/1997 |
| RU | 2099078 | 12/1997 |
| RU | 2303373 | 7/2007 |
| WO | WO94/02036 | 2/1994 |
| WO | WO98/04361 | 2/1998 |
| WO | WO98/41113 | 9/1998 |
| WO | WO98/43617 | 10/1998 |
| WO | WO98/57627 | 12/1998 |
| WO | WO99/66913 | 12/1999 |
| WO | WO00/02553 | 1/2000 |
| WO | WO00/11968 | 3/2000 |
| WO | WO00/30666 | 6/2000 |
| WO | WO00/44375 | 8/2000 |
| WO | WO00/48594 | 8/2000 |
| WO | WO00/49891 | 8/2000 |
| WO | WO01/17366 | 3/2001 |
| WO | WO01/21208 | 3/2001 |
| WO | WO01/58271 | 8/2001 |
| WO | WO02/35943 | 5/2002 |
| WO | WO02/45525 | 6/2002 |
| WO | WO 02/052955 | 7/2002 |
| WO | WO 02/071874 | 9/2002 |
| WO | WO03/035056 | 5/2003 |
| WO | WO2005/006877 | 1/2005 |
| WO | WO2005/013714 | 2/2005 |
| WO | WO2005/058064 | 6/2005 |
| WO | WO2006/058248 | 6/2006 |
| WO | WO2006/058278 | 6/2006 |
| WO | WO2006/069241 | 6/2006 |
| WO | WO2006/071919 | 7/2006 |
| WO | WO2006/074089 | 7/2006 |
| WO | WO2007/009111 | 1/2007 |
| WO | WO2007/022344 | 2/2007 |
| WO | WO2007/063095 | 6/2007 |
| WO | WO2007/094669 | 8/2007 |
| WO | WO2007/149815 | 12/2007 |
| WO | WO2008/151131 | 12/2008 |
| WO | WO2010/083409 | 7/2010 |
| ZA | 9605149 A | 1/1997 |

OTHER PUBLICATIONS

Brigelius-Flohe et al 1999, "Vitamin E. Function and Metabolism," FASEB J. 13:1145-1155.

Cao et al., 1998, "Increases in Human Plasma Antioxidant Capacity after Consumption of Controlled Diets High in Fruit and Vegetables," Amer. J. Clin, Nutr. 68:1081-1087.

Cotman et al., 2002, "Brain Aging in the Canine: A Diet Enriched in Antioxidants Reduces Cognitive Dysfunction," Neurobiol. Of Aging 23(5):809-818.

Cummings et al., 1996, "The Canine As an Animal Model of Human Aging and Dementia," Neurobiol. Of Aging 17:259-268.

Dodd et al., 2003, "Can a Fortified Food Affect Behavioral Manifestations of Age-Related Cognitive Decline in Dogs?" Veterinary Medicine 98:396-408.

Estrada et al., 2001, "The Effects of Diet and Age on the Performance of the Landmark Discrimination Learning Task," 31st Ann. Meeting of Soc. For Neurosci., San Diego, CA 27(1):279, Abstract Biosis AN: PREV200100472166.

Frei, 1999, "Molecular and Biological Mechanisms of Antioxidant Action," FASEB J. 13:963-964.

Harman, 1993, "Free Radical Theory of Aging: A Hypothesis on Pathogenesis of Senile Dementia of the Alzheimer's Type," Age 16:23-30.

Head et al., 1995, "Spatial Learning and Memory as a Function of Age in the Dog," Behavioral Neurosa 109(5):851-858.

Head et al., 2002, "A Longitudinal Dietary Antioxidant Intervention in Aged Canines Improves Learning and Reduces Peripheral Measures of Oxidative Damage," 32nd Annual Meeting of Soc. For Neurosci., Orlando, FL Biosis AN:PREV200300381007.

Ikeda-Douglas et al., 2004, "Prior Experience, Antioxidants, and Mitochondrial Cofactors Improve Cognitive Function in Aged Beagles," Vet. Then 5(1):5-16.

International Search Report and Written Opinion in International Application No. PCT/US05/047192, mailed Jun. 14, 2000.

Joseph, 2009, "Nutrition, Brain Aging, and Neurodegeneration," J. Neurosci. 29(41):12795-12801.

Leveque, 1998, "Cognitive Dysfunction in Dogs, Cats an Alzheimer's-Like Disease," J. Amer. Vet. Med. Assoc. 212(9):1351.

Lovell et al., 1998, "Elevated 4-Hydroxynonenal in Ventricular Fluid in Alzheimer's Disease," Neurobiol. Of Aging 18:457-461.

Markesbery et al., 1998, "Four-Hydroxnonenal, a Product of Lipid Peroxidation, Is Increased in the Brain in Alzheimer's Disease," Neurohiol. Of Aging 19:31-36.

Milgram et al., 1994, "Cognitive Functions and Aging in the Dog: Acquisition of Nonspatial Visual Tasks," Behavioral Neurosci. 108(1):57-68.

Milgram et al., 1999, "Landmark Discrimination Learning in the Dog," Learning & Memory 6(1):54-61.

Milgram et al., 2002, "Dietary Enrichment Counteracts Age-Associated Cognitive Dysfunction in Canines." Neurobiol. Of Aging 23(5):737-745.

Milgram et al.. 2002, "Landmark Discrimination Learning in the Dog: Effects of Age, an Antioxidant Fortified Food, and Cognitive Strategy," Neurosci. Biobehav. Rev. 26(6):679-695.

Milgram et al., 2004, "Long-Term Treatment with Antioxidants and a Program of Behavioral Enrichment Reduces Age-Dependent Impairment in Discrimination and Reversal Learning in Beagle Dogs," Exp. Gerontol. 39(5):753-765.

Milgram et al., 2005, "'Learning Ability in Aged Beagle Dogs is Preserved by Behavioral Enrichment and Dietary Fortification: A Two-Year Longitudinal Study," Neurobiology of Aging 26(1):77-90.

Sang et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.

Siwak et al., 2003, "Locomotor Activity Rythms in Dogs Vary with Age and Cognitive Status," Behavioral Neurosci. 117(4):813-824.

Syufy, 2007, "Q. How Long Is the Common Cat Supposed to Live?" http://cats.about.com/cs/catmanagement101/f/lifespan_cats.htm website retrieved Nov. 12, 2007.

Tapp et al., 2003, "An Antioxidant Enriched Diet Improves Concept Learning in Aged Dogs," 33rd Annual Meeting of Soc. For Neurosci., New Orleans, LA Biosis AN: PREV200400205135.

Vazour, 2012, "Dietary Polyphenols as Modulators of Brain Functions: Biological Actions and Molecular Mechanisms Underpinning Their Beneficial Effects," Oxidative Med. And Cell. Longevity vol. 2012, Article ID: 914273, 16 pgs.

Anonymous, 2009, Dogs and Cats—Different Species, Different Needs, Retrieved from the internet http://www.felinefuture.com/?p=521, pp. 1-4.

AAFCO, 2004, American Association of Feed Control Officials Official Publication pp. 129-137.

Amazon.Com, 2007, "Hill's Science Diet Canine Senior" www.amazon.com website.

Ames et al., 1993, "Oxidants, Antioxidants and the Degenerative Diseases of Aging," Proc. Natl. Acad. Sci. 90(17):7915-7922.

Ames, 1998, "Micronutrients Prevent Cancer and Delay Aging," Toxicol. Lett. 102-103:5-18.

Arivazhagan et al., 2000, "Antioxidant Lipoate and Tissue Antioxidants in Aged Rats," J. Nutr. Biochem. 11(3):122-127.

Arivazhagan et al., 2001, "Effect of DL-α-Lipoic Acid on the Status of Lipid Peroxidation and Antioxidants in Mitochondria of Aged Rats," J. Nutr. Biochem. 12:2-6.

Aksenova et al., 1999, "Oxidation of cytosolic proteins and expression of creatine kinase BB in frontal lobe in different neurodegenerative disorders," Dement. Geriatr. Cogn. Disord. 10(2):158-165.

Austad, 2008, "Advances in Vertebrate Aging Research 2007," Aging Cell 7(2):119-124.

Beckman et al., 1998, "Mitochondrial Aging: Open Questions," Annals NY Acad. Sci. 854:118-127.

Beckman et al., 1998, "The Free Radical Theory of Aging Matures," Physiol. Rev. 78(2):547-581.

Berkson, 1999, "A conservative triple antioxidant approach to the treatment of hepatitis C. Combination of alpha lipoic acid (thioctic acid), silymarin, and selenium: three case histories," Med. Klin 94(Suppl. 3):84-89 Medline AN: NLM10554539 Abstract.

Bezlepkin et al., 1996, "The prolongation of survival in mice by dietary antioxidants depends on their age by the start of feeding this diet," Mech. Ageing Dev. 92(2-3):227-234.

Bickford et al., 2000, "Antioxidant-rich diets improve cerebellar physiology and motor learning in aged rats," Brain Res. 866(1-2):211-217.

Blagosklonny, 2007, "An anti-aging drug today: from senescence-promoting genes to anti-aging pill," Drug Discovery Today 12(5/6):218-224.

Borras et al., 1999, "Age-related changes in the brain of the dog," Vet. Pathol. 36(3):202-211.

Branam, 1987, "Dietary Management of Geriatric Dogs and Cats," Vet. Tech. Vet. Learning Syst. 8(10):501-503.

Bruce-Keller et al., 1998, "4-Hydroxynonenal, a product of lipid peroxidation, damages cholinergic neurons and impairs visuospatial memory in rats," J. Neuropathol. And Exp. Neurol. 57(3):257-267.

Cantuti-Castelvetri et al., 2000, "Neurobehavioral Aspects of Antioxidants in Aging," Int. J. Develop. Neurosci. 18(4-5):367-381.

Caprioli et al., 1990, "Age-dependent deficits in radial maze performance in the rat: effect of chronic treatment with acetyl-L-carnitine," Prog. Neuro-Psychopharmacol. & Biol. Psychiat. 14(3):359-369.

Chandra, 2001, "Effect of vitamin and trace-element supplementation on cognitive function in elderly subjects," Nutrition 17(9):709-712.

Christen, 2000, "Oxidative stress and Alzheimer disease," Amer. J. Clin. Nutr. 71(2):621S-629S.

Coe, 2012, "Osteoarthritis in Dogs," http://www.vetbase.co.uk/information/osteoarthritis-dogs.php.

Crayhon, 1998, "Real Power of Antioxidants," Total Health 20(2):27-35.

Cutler, 1991, "Antioxidants and Aging," Amer. J. Clin. Nutr. 53(Suppl. 1):373S-379S.

Dictionary.com, 2012, Definition for "Prevent".

Droge, 2003, "Oxidative stress and aging," Adv. Exp. Med. Biol. 543:191-200.

Dunn, 2009, "Cats Are Different," Retrieved from the internet http://www.catsofaustralia.com/cat-nutrition.htm, p. 104.

Dzanis, 1994, "The Association of American Feed Control Officials Dog and Cat Food Nutrient Profiles: substantiation of nutritional adequacy of complete and balanced pet foods in the United States," J. Nutr. 124(12 Suppl):25355-25395.

Emmons, 1999, "Antioxidants to the Rescue," South Bend Tribune pp. 1-4.

Epinions.com, 2000, "Science Diet Senior Dry: The Healthiest on the Shelf!!!!" Epinions.com website.

Ernst, 1999, "Diet and Dementia, Is There a Link? A Systemati Review," Nutr. Neurosci. 2:1-6.

Fryer, 1998, "Vitamin E Status and Neurodegenerative Disease," Nutritional Neurosci. 1(5):327-351.

Fuchs et al., 1994, "Antioxidant inhibition of skin inflammation induced by reactive oxidants: evaluation of the redox couple dihydrolipoate/lipoate," Skin Pharmacol. 7(5):278-284.

Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.

Gabbita et al., 1998, "Increased nuclear DNA oxidation in the brain in Alzheimer's disease," J. Neurochem. 71(5):2034-2040.

Grundman, 2000, "Vitamin E and Alzheimer disease: the basis for additional clinical trials," Amer. J. Clin. Nutr. 71(2):630S-636S.

Hagen et al., 1999, "(R)-alpha-lipoic acid-supplemented old rats have improved mitochondrial function, decreased oxidative damage, and increased metabolic rate," FASEB J. 13(2):411-418.

Han et al., 1997, "Lipoic acid increases de novo synthesis of cellular glutathione by improving cystine utilization," BioFactors 6(3):321-338.

Harman, 1961, "Prolongation of the normal lifespan and inhibition of spontaneous cancer by antioxidants," J. Gerontol. 16:247-254.

Hawthorne, 2002, "Nutritional Requirements of Aging Dogs and Cats," Waltham Focus 12(1):28-34.

Hill et al., 2004, "Lipoic acid is 10 times more toxic in cats than reported in humans, dogs or rats," J. Animal Physiol. A. Animal Nutrition 88(3-4):150-156.

Information Network Village, 2011, Specialties (Agricultural Produce) http://www.invil.org/english/specialty/vegetable/potato/contents.jsp?con_no=602519&page_no=1.

International Search Report and Written Opinion in International Application No. PCT/US01/048495, mailed Jul. 30, 2002.

International Search Report and Written Opinion in International Application No. PCT/US01/049654, mailed Jul. 30, 2002.

International Search Report and Written Opinion in International Application No. PCT/US06/027615, mailed Nov. 22, 2006.

International Search Report and Written Opinion in International Application No. PCT/US09/058244, mailed Dec. 14, 2009.

International Search Report and Written Opinion in International Application No. PCT/US09/068166, mailed May 7, 2010.

International Search Report and Written Opinion in International Application No. PCT/US09/068244, mailed Feb. 18, 2010.

International Search Report and Written Opinion in International Application No. PCT/US09/069686, mailed Nov. 12, 2010.

International Search Report and Written Opinion in International Application No. PCT/US10/041888, mailed Nov. 12, 2010.

Jayachandran et al., 1996, "Status of lipids, lipid peroxidation, and antioxidant systems with Vitamin C supplementation during aging in rats," J. Nutritional Biochem. 7(5):270-275.

Jones et al., 1997, "Evidence for the involvement of docosahexaenoic acid in cholinergic stimulated signal transduction at the synapse," Neurochemical Research 22(6):663-670.

Joseph et al., 2000, "Oxidative stress protection and vulnerability in aging: putative nutritional implications for intervention," Mechanisms of Ageing and Development 116(2-3):141-153.

Kalaiselvi et al., 1998, "Effect of L-Carnitine on the Status of Lipid Peroxidation and Antioxidants in Aging Rats," J. Nutr. Biochem. 9:575-581.

Kealy et al., 2002, "Effects of diet restriction on life span and age-related changes in dogs," J. Amer. Vet. Med. Assoc. 220(9):1315-1320.

Keller et al., 1999, "4-hydroxynonenal increases neuronal susceptibility to oxidative stress," J. Neurosci. Res. 58(6):823-830.

Kim et al., 2006, "Antioxidant alpha-lipoic acid inhibits osteoclast differentiation by reducing nuclear factor-kappaB DNA binding and prevents in vivo bone resorption induced by receptor activator of nuclear factor-kappaB ligand and tumor necrosis factor-alpha," Free Radical Biol. & Med. 40(9):1483-1493.

Kolb et al., 1997, "Zum Bedarf an Vitaminen and an Ascorbinsaure beim Hund, mit Bemerkungen zur Publikation von M. Torel, TU51, 785-790, 996," Tieraerztliche Umschau 52(12):728-733.

Lee et al., 2004, "The impact of alpha-lipoic acid, coenzyme Q10 and caloric restriction on life span and gene expression patterns in mice," Free Radical Biol. Med. 36(8):1043-1057.

Liu et al., 1999, "Stress, aging, and brain oxidative damage," Neurochem. Res. 24(11):1479-1497.

Lovell et al., 1999, "Increased DNA oxidation and decreased levels of repair products in Alzheimer's disease ventricular CSF," J. Neurochem. 72(2):771-776.

Markesbery et al., 1999, "Oxidative alterations in Alzheimer's disease," Brain Pathol. 9(1):133-146.

McGahon et al., 1999, "Age-related changes in oxidative mechanisms and LTP are reversed by dietary manipulation," Neurobiology of Aging 20(6):643-653.

McGahon et al., 1999, "Age-related changes in LTP and antioxidant defenses are reversed by an alpha-lipoic acid-enriched diet," Neurobiology of Aging 20(6):655-664.

McGahon et al., 1999, "Age-related changes in synaptic function: analysis of the effect of dietary supplementation with omega-3 fatty acids," Neuroscience 94(1):305-314.

Melder, 1982, "Modulation of natural killer cell activity in mice after interferon induction: depression of activity and depression of in vitro enhancement by interferon," Infect. Immun. 36(3):990-995.

Milgram et al., 2000, "Landmark Discrimination Learning in Aged Dogs Is Improved by Treatment with an Antioxidant Enriched Diet," Poster Presentation No. 193.9 at Society for Neuroscience Meeting New Orleans, LA.

Milgram et al., 2001, "Age Dependent Cognitive Dysfunction in Canines: Dietary Intervention," Proc. Of the Third International Conference on Veterinary Behavioural Medicine, Overall, ed., Universities Federation for Animal Welfare, publisher pp. 53-57.

Milgram et al., 2007, "Acetyl-L-carnitine and alpha-lipoic acid supplementation of aged beagle dogs improves learning in two landmark discrimination tests," FASEB J. 21(13):3756-3762.

Nourhashemi et al., 2000, "Alzheimer disease: protective factors," Amer. J. Clin. Nutr. 71(2):6435-6495.

Packer et al., 1995, "alpha-Lipoic acid as a biological antioxidant," Free Radical Biol. & Med. 19(2):227-250.

Packer et al., 1997, "Neuroprotection by the metabolic antioxidant alpha-lipoic acid," Free Radical Biol. & Med. 22(1-2):359-378.

Pastuszka et al., 2007, "Alpha-lipoic acid may be a clinically useful therapy in interstitial cystitis," Medical Hypotheses 69(4):957-958.

Patrick, 2000, "Nutrients and HIV: part three-N-acetylcysteine, alpha-lipoic acid, L-glutamine, and L-carnitine," Alt. Med. Review 5(4):290-305.

Perkins et al., 1999, "Association of antioxidants with memory in a multiethnic elderly sample using the Third National Health and Nutrition Examination Survey," Amer. J. Epidemiol. 150(1):37 44.

Petsonthepark.com 2007 "Science Diet Large Breed Senior 8kg," www.petsonthepark.com.au.prod207.htm.

Petwave.com, 2012, "Treamtment [sic] & Prognosis of Renal Dysplasia in Dogs".

Podda et al., 1994, "Alpha-lipoic acid supplementation prevents symptoms of vitamin E deficiency," Biochem. Biophys. Res. Commun 204(1):98-104.

Pratico et al., 1998, "Increased F2-isoprostanes in Alzheimer's disease: evidence for enhanced lipid peroxidation in vivo," FASEB J. 12(15):1777-1783.

Pugh et al., eds., 2000, Stedman's Medical Dictionary, 27th Edition, Williams & Wilkins, p. 377.

Radak et al., 2001, "Regular exercise improves cognitive function and decreases oxidative damage in rat brain," Neurochem. International 38(1):17-23.

Riedel et al., 1998, "Nutrients, age and cognitive function," Curr. Opin. Nutr. Metab. Care 1(6):579-585.

Rogers, 2001, "A healthy body, a healthy mind: long-term impact of diet on mood and cognitive function," Proceedings of the Nutrition Society 60(1):135-143.

Rosenberg et al., 1959, "Effect of α-lipoic acid on vitamin C and vitamin E deficiencies," Arch. Biochem. Biophys. 80(1):86-93.

Roy et al., 1998, "Redox regulation of cell functions by alpha-lipoate: biochemical and molecular aspects," BioFactors 7(3):263-267.

Roy et al., 1998, "Redox regulation of cell functions by alpha-lipoate: biochemical and molecular aspects," BioFactors 8(1-2):17-21.

Ruehl et al., 1998, "Canine Cognitive Dysfunction," Ch. 13 in: *Psychopharmacology of Animal Behavior Disorders*, Wiley-Blackwell, publisher, Dodman et al., eds., pp. 283-304.

Ruvo et al., 2000, "Nutritional antioxidants as antidegenerative agents," Int. J. Developmental Neurosci. 18(4-5):359-366.

Rybak et al., 1999, "Dose dependent protection by lipoic acid against cisplatin-induced ototoxicity in rats: antioxidant defense system," Toxicol. Sci. 47(2):195-202.

Sastre et al., 1998, "A Ginkgo biloba extract (EGb 761) prevents mitochondrial aging by protecting against oxidative stress," Free Radical Biol. Med. 24(2):298-304.

Savitha et al., 2005, "Oxidative stress on mitochondrial antioxidant defense system in the aging process: role of DL-alpha-lipoic acid and L-carnitine," Clinica Chimica Acta 355(1-2):173-180.

Schoenherr et al., 1997, "Nutritional modification of inflammatory diseases," Seminars in Veterinary Medicine and Surgery (Small Animal) 12(3):212-222.

Schupke et al., 2001, "New metabolic pathways of alpha-lipoic acid," Drug Metab. Dispos. 29(6):855-862.

Shigenaga et al., 1994, "Oxidative damage and mitochondrial decay in aging," PNAS 91(23):10771-10778.

Siwak et al., 2000, "Age-associated changes in non-cognitive behaviors in a canine model of aging," Soc. Neurosci. 26(2):2332, Abstract No. 873.3.

Siwak et al., 2005, "Chronic antioxidant and mitochondrial cofactor administration improves discrimination learning in aged but not young dogs," Progress in Neuro-Psychopharmacol. Biological Psychiatry 29(3):461-469.

Socci et al., 1995, "Chronic antioxidant treatment improves the cognitive performance of aged rats," Brain Research 693(1-2):88-94.

Stoll et al., 1993, "The potent free radical scavenger alpha-lipoic acid improves memory in aged mice: putative relationship to NMDA receptor deficits," Pharmacol. Biochem. & Behavior 46(4):799-805.

Stoll et al., 1994, "The potent free radical scavenger alpha-lipoic acid improves cognition in rodents," Ann. NY Acad. Sci. 717:122-128.

Tsokos et al., 1982, "Natural killer cells and interferon responses in patients with systemic lupus erythematosus," Clin. Exp. Immunol. 50(2):239-245.

Vancouver Vets, 2011, "Osteoarthritis in Dogs. Treatment & Prognosis" www.articlesbase.com/print/5146156.

Villeponteau et al., 2000, "Nutraceutical interventions may delay aging and the age-related diseases," Exp. Gerontol. 35(9-10):1405-1417.

Weaver et al., 1988, "Health effects and metabolism of dietary eicosapentaenoic acid," Prog. Food Nutr. Sci. 12(2):111-150.

Youdim et al., 2000, "Essential fatty acids and the brain: possible health implications," Int. J. Devel. Neurosciences 18(4-5):383-399.

* cited by examiner

METHODS FOR INHIBITING A DECLINE IN LEARNING AND/OR MEMORY IN ANIMALS

CROSS-REFERENCE TO RELATED APPLICATIONS

This application claims priority to U.S. Provisional Application Ser. No. 60/639,928, filed Dec. 22, 2004, and to U.S. Provisional Application Ser. No. 60/669,097, filed Apr. 7, 2005, the disclosures of which is incorporated herein by reference.

BACKGROUND OF THE INVENTION

1. Field of the Invention

The present invention relates generally to methods for inhibiting a decline in learning and/or memory in animals and particularly to methods for using antioxidants inhibiting a decline in learning and/or memory in canine and feline animals.

2. Description of the Related Art

In designing foods for animals such as dogs and cats, optimal physical health through good nutrition is an important goal. However, a diet which meets ordinary physical nutritional requirements may not be enough to provide the best nutrition for maximizing cognitive function, including learning and memory.

Dogs, cats, and many other animals are required to utilize their cognitive skills for many purposes in their interactions with humans, other animals and/or their environment. For example, working dogs (such as police dogs and guard dogs), hunting dogs, herding dogs (including sheepdogs), guide dogs, show dogs and search and rescue dogs are expected to demonstrate even higher levels of cognitive skills than dogs kept only as pets. Dogs and other animals of any age can demonstrate declines in learning ability and memory, resulting in frustration on the part of the owner or caregiver of the animal and the animal.

Decline in memory and learning ability in animals has largely been accepted as part of the cost of working and living with animals. Such declines are generally age-related and become most noticeable in aged and geriatric animals, but can also be an important limitation to the usefulness of working animals such as dogs and the enjoyment and companionship provided by pets and other in their young adult years, for example from about 1 to about 6 years of age. Given the problem, there is a need for new methods for inhibiting a decline in learning and/or memory in animals such as dogs and cats.

SUMMARY OF THE INVENTION

The invention provides methods for inhibiting a decline in learning and/or memory in animals, particularly canines and felines such as dogs and cats, by maintaining the animal on an antioxidant-fortified diet comprising a decline in learning and/or memory inhibiting amount of at least one antioxidant for a period of at least about 3 years. The methods are useful for animals such as canines and felines of any breed of occupation but are particularly useful for dogs and cats that rely on maintenance of cognitive functions such as learning and memory during their adult years for effectiveness or quality of companionship or for providing useful services to their owner or caregiver.

Additional or alternative advantages and benefits of the present method will be apparent to one skilled in the art from reading this specification.

DETAILED DESCRIPTION OF THE INVENTION

Definitions

The term "animal" means any animal susceptible to or suffering from a decline in learning and/or memory, particularly resulting from aging.

A "young adult" animal for a canine or feline means a canine or feline of about 1 to about 6 years of age. For other animal species, the age range for a "young adult" will vary according to the species, but will be known to skilled artisans.

The phrase "total antioxidant amount" stated herein as being effective for a given function, e.g., to inhibit decline in learning and/or memory, refers to an amount in total of all antioxidants, or according to the context all specified antioxidants, present in or added to the diet. If only one antioxidant is present, the "total antioxidant amount" is the amount of that one antioxidant.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual antioxidants physically associated such that they are considered a unit for manufacture, distribution, sale, or use.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The Invention

The invention provides methods for inhibiting a decline in learning and/or memory in animals. The methods comprise maintaining the animal on an antioxidant-fortified diet comprising a decline in learning and/or memory inhibiting amount of at least one antioxidant for a period of at least about 3 years. The methods surprisingly inhibit a decline in learning and/or memory in animals and increase their mental capacity.

The methods of the invention are useful for a variety of human and non-human animals, including avian, bovine, canine, equine, feline, hicrine, murine, ovine, and porcine animals, and are particularly useful for companion animals such as canines and felines, including dogs and cats.

In one embodiment, the animal is a canine and the diet comprises at least one antioxidant selected from the group consisting of vitamin E, vitamin C, α-lipoic acid, and combinations thereof. In another, the animal is a feline and the diet comprises at least one antioxidant selected from the group consisting of vitamin E, vitamin C, and combinations thereof. In either embodiment, the diet may further comprise plant meal such as fruit meal and/or vegetable meal.

The methods are especially useful for dogs maintained on the fortified diet for an extended period. The benefit will become greater the longer the dog is maintained on the fortified diet. For example, maintaining the dog on such a diet for a period of at least about 4 years or a period of at least about 5 years or for substantially the duration of the dog's adult life can further enhance the benefits obtained.

In some embodiments, a single antioxidant is present in the diet. In others, a plurality of antioxidants is present in the diet.

Antioxidants useful in the present invention include any substance that is capable of reacting with free radicals and neutralizing them. Illustrative examples of such substances include β-carotene, selenium, coenzyme $Q_{10}$ (ubiquinone), luetin, tocotrienols, soy isoflavones, S-adenosylmethionine, glutathione, taurine, N-acetylcysteine, vitamin E, vitamin C, α-lipoic acid and L-carnitine. Examples of foods containing useful levels of one or more antioxidants include but are not limited to *ginkgo biloba*, green tea, broccoli, citrus pulp, grape pomace, tomato pomace, carrot, spinach, and a wide variety of fruit meals and vegetable meals.

Except where the context demands otherwise, the term "vitamin E" is used generically herein to encompass any tocopherol or tocotriene compound, including any enantiomer or racemate thereof, and any mixture of such compounds, having vitamin E activity, including α-tocopherol ((+)-2,5,7,8-tetramethyl-2-(4,8,12-trimethyltridecyl)-6-chromanol), β-tocopherol ((+)-2,5,8-trimethyl-2-(4,8,12-trimethyltridecyl)-6-chromanol), γ-tocopherol ((+)-2,7,8-trimethyl-2-(4,8,12-trimethyltridecyl)-6-chromanol), δ-tocopherol ((+)-8-methyl-2-(4,8,12-trimethyltridecyl)-6-chromanol), α-tocotrienol (2,5,7,8-tetramethyl-2-(4,8,12-trimethyl-3,7,11-tridecatrienyl)-6-chromanol) and β-tocotrienol (2,5,8-trimethyl-2-(4,8,12-trimethyl-3,7,11-tridecatrienyl)-6-chromanol). Vitamin E can be administered as any one or a mixture of the above compounds or in the form of various derivatives thereof such as esters, including vitamin E acetate, succinate, palmitate and the like, that exhibit vitamin E activity after ingestion by the animal. Typically vitamin E as used in the present method comprises α-tocopherol or an ester thereof.

Vitamin C can be administered as ascorbic acid, e.g., L-ascorbic acid, or as various derivatives thereof such as calcium phosphate salt, cholesteryl salt, and ascorbate-2-monophosphate. Salts of vitamin C include, for example, sodium salt, calcium salt, zinc salt and ferrous salt. Esters include, for example, stearate, palmitate and like derivatives. Vitamin C or a derivative thereof can be in any physical form, for example, a liquid, a semisolid, a solid, or a heat stable form that exhibits vitamin C activity after ingestion by the animal.

Lipoic acid can be administered as such, as a lipoate salt or ester, or as a lipoate derivative, for example as described in U.S. Pat. No. 5,621,117. As used herein, "lipoic acid" is synonymous with α-lipoic acid and can be provided in various forms including racemic mixtures, salts, esters and/or amides thereof.

Antioxidants can be added to the diet as antioxidant substances per se (including derivatives thereof having antioxidant activity), such substances being of natural, biosynthetic or chemosynthetic origin. Alternatively or in addition, antioxidants can be added as components of food ingredients such as those listed above.

In some embodiments, including animals with life spans greater than about 15 years, the animal is maintained on the antioxidant-fortified diet for a period of greater than 3 years, e.g., for a period of at least about 4 years or a period of at least about 5 years.

In one embodiment, the method comprises maintaining a dog on an antioxidant-fortified diet for a period of at least about 3 years, wherein the diet comprises at least one antioxidant and further comprises fruit and/or vegetable meal.

Diets include food compositions such as canned moist foods, extruded dry foods, supplements and treats, having the antioxidant as an ingredient thereof. Any food component of the diet can benefit from inclusion of an antioxidant as defined herein, but in one embodiment the food is one having a major (at least about 25%, for example at least about 50%, by weight) component derived from animal (e.g., mammal, bird, fish or seafood) proteinaceous tissues including muscle tissues and/or offal, optionally with a carbohydrate source such as cereal grains.

The antioxidant(s) such as vitamin E, vitamin C, α-lipoic acid and/or plant meal can be distributed more or less homogeneously through a food component of the diet. Alternatively, the antioxidant(s) can be present in a food component of the diet in whole or in part on surfaces of food pieces such as meat chunks, dry kibbles or individual treats such as biscuits.

The antioxidant(s) such as vitamin E, vitamin C, α-lipoic acid and/or plant meal should be present in an amount that is not toxic or otherwise deleterious to the health of an animal consuming a normal quantity of the food composition. In particular, the antioxidant(s) should be present at a concentration that does not cause undesirable effects on digestion, particularly long-term effects lasting several days or longer. Undesirable effects on digestion can include constipation or diarrhea.

An animal can be maintained on the antioxidant-fortified diet by feeding the antioxidant or mixture of antioxidants as a component of the animal's food or as a food supplement. The quantities provided in the food, all on a dry matter basis, are stated herein as the active material, i.e., measured as the free antioxidant substance. The antioxidant amount should not exceed a maximum above which toxicity is brought about. The antioxidant, or combination thereof, is fed to the animal in a total antioxidant amount effective to inhibit decline in learning and/or memory. What constitutes an effective amount varies depending on the breed and activity of the animal, the type of antioxidant(s) and other factors. One of skill in the art will, by routine testing based on the disclosure herein, readily establish a total antioxidant amount effective to inhibit decline in learning and/or memory in any particular situation.

Suitable amounts of vitamin E will normally be at least about 10 parts per million (ppm), more generally at least about 100 ppm, illustratively about 100 ppm to about 5000 ppm, about 150 ppm to about 2500 ppm, or about 200 ppm to about 1500 ppm, for example about 500 ppm to about 1000 ppm.

Suitable amounts of vitamin C will normally be at least about 5 ppm, more generally at least about 10 ppm, illustratively about 10 ppm to about 10,000 ppm, about 20 ppm to about 2000 ppm, or about 25 ppm to about 500 ppm, for example about 50 ppm to about 500 ppm or about 75 ppm to about 500 ppm.

Suitable amounts of α-lipoic acid will normally be at least about 5 ppm, more generally at least about 25 ppm, illustratively about 25 ppm to about 1000 ppm, or about 50 ppm to about 600 ppm, for example about 100 ppm to about 600 ppm.

Suitable amounts of plant meal will depend on its antioxidant content, determined for example as Trolox equivalent. Illustratively, a plant meal with an antioxidant content of at least about 25 μmol Trolox equivalents per gram of dry matter, or a combination of such plant meals, can be added to a diet at about 1% to about 5% by weight. Examples of plant meals having suitable antioxidant content include spinach pomace, tomato pomace, citrus pulp, grape pomace, carrot granules, broccoli, green tea, *ginkgo biloba* and corn gluten meals.

In one embodiment, the food further comprises one or more ingredients other than an antioxidant that, in combination with the antioxidant, can inhibit a decline in learning and/or memory in animals such as young adult dogs and cats.

An example of such an ingredient is an omega-3 fatty acid such as eicosapentaenoic acid (EPA) or docosahexaenoic acid (DHA).

Where the antioxidant is localized on surfaces of food pieces, local concentrations can exceed those suggested here, but the overall concentration in the diet as a whole will generally be in a range as stated above.

In preparing a food useful according to the present invention, the components of the food are adjusted so that the antioxidant, for example vitamin E, vitamin C, α-lipoic acid and/or plant meal, is present in the food at a desired concentration. The antioxidant(s) can, for example, be incorporated into the food during formulation, such as during and/or after mixing of other components of the composition. Distribution of these components into the composition can be accomplished by any conventional method including standard mixing procedures.

Foods useful in the method of the invention can be prepared in a wet or containerized (e.g., canned or in pouches) form using conventional pet food processes. In one embodiment, ground animal (e.g., mammal, poultry, fish and/or seafood) proteinaceous tissues are mixed with other ingredients, including for example animal fats and vegetable oils, cereal grains, other nutritionally balancing ingredients, special purpose additives (e.g., vitamin and mineral mixtures, inorganic salts, cellulose and beet pulp, bulking agents, and the like); and water sufficient for processing is also added. These ingredients typically are mixed in a vessel suitable for heating while blending the components. Heating of the mixture can be effected in any suitable manner, such as, for example, by direct steam injection or by using a vessel fitted with a heat exchanger. Following addition of the last of these ingredients, the mixture is heated in a pre-cooking step to a temperature of up to about 100° C. Higher temperatures can be acceptable, but can be commercially impractical without use of other processing aids. When heated to the appropriate temperature, the material is typically in the form of a thick liquid. The thick liquid is filled into suitable containers such as cans, jars, pouches or the like. A lid is applied, and the container is hermetically sealed. The sealed containers are then placed into conventional equipment designed to sterilize the contents. This is usually accomplished by heating to a temperature of at least about 110° C. for an appropriate time, which is dependent on, for example, the temperature used and the composition. Products can also be prepared by an aseptic process wherein the contents are heated to commercial sterility before being packaged in sterilized containers.

The antioxidant(s) can be added to containerized food products before, during or after the pre-cooking step.

Foods useful in the method of the invention can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, minerals, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which can include, for example, flavors, fats, oils, powders, and the like. Kibble also can be made from the dough using a baking process, rather than extrusion, wherein the dough is placed into a mold before dry-heat processing. Kibble also can be made from a food matrix undergoing pelletization.

The antioxidant(s) can be incorporated into the food by addition to the above-described mixtures before extrusion or by coating extruded kibble or pellets with the antioxidant(s) as an ingredient of a topical coating. For example, vitamin E can be added to liquids in a dry processing line, to a pre-conditioner composition or to a coating composition.

In another embodiment, a food useful according to the present method is a treat comprising at least one antioxidant, for example vitamin E, vitamin C, α-lipoic acid and/or plant meal. Treats include, for example, foods that are given to an animal to entice the animal to eat during a non-meal time. Treats for canines include biscuits, for example in the shape of dog bones. Treats can be nutritional, comprising one or more nutrients, and can, for example, comprise ingredients as described above for a food. Non-nutritional treats encompass any other treats that are non-toxic. The antioxidant(s) can be present in a coating on the surface of the treat, or incorporated into the treat, or both. Plant meal if present is typically incorporated into the treat.

In another embodiment, a food useful according to the present method is a nutritional supplement comprising at least one antioxidant, for example vitamin E, vitamin C, α-lipoic acid and/or plant meal, as defined herein. Supplements include, for example, a food used with another food to improve the nutritive balance or performance of the total. Supplements include foods that are fed undiluted as a supplement to other foods, offered free choice with other parts of an animal's diet that are separately available, or diluted and mixed with an animal's regular food to produce a complete diet. The AAFCO, for example, provides a discussion relating to supplements in the American Feed Control Officials, Inc. Official Publication (2003), at p. 220. Supplements can be in various forms including, for example, powders, liquids, syrups, pills, encapsulated compositions, etc.

Antioxidants such as vitamin E, vitamin C and α-lipoic acid can be encapsulated in food systems. For example, vitamin E can be added to a palatant (such as a digest or broth) at any time during processing of the palatant.

Antioxidants such as vitamin E, vitamin C, α-lipoic acid and/or plant meal can be added during manufacturing of the food, for example by a process of mixing or coating as indicated above. In one embodiment, the antioxidant(s) are added to an animal's food by the person responsible for feeding the animal. For this purpose, the antioxidant(s) can be added in diluted or dispersed form in a suitable carrier such as vegetable oil or edible powder as it is more convenient and reduces risk of accidental over-addition of the antioxidant. A powder comprising the antioxidant(s) can be sprinkled on an animal's food immediately before feeding. Alternatively, a liquid comprising the antioxidant(s) can be sprayed on the food. Such powder or liquid compositions are described herein as "antioxidant compositions" and can be thought of as "additives". They can be applied to the top of a serving of food and/or can, if desired, be mixed into the food. The use of antioxidant compositions or additives, for example comprising vitamin E, vitamin C, α-lipoic acid and/or plant meal, as specified herein to inhibit decline in learning and/or memory in young adult dogs is an embodiment of the present invention. Accordingly there is provided herein a method for inhibiting a decline in learning and/or memory in a young adult dog, the method comprising adding to a food component of the diet of the dog an antioxidant composition that comprises a powder or liquid carrier having the antioxidant diluted or dispersed therein, and maintaining the dog on the diet for a period of at least about 3 years. A total antioxidant amount effective for inhibiting a decline in learning and/or memory, when added as an antioxidant composition to a food according to the present embodiment, will generally be found in a range as provided herein.

In a further embodiment, there is provided a method for inhibiting a decline in learning and/or memory in a dog comprising maintaining the dog on an antioxidant-fortified diet for a period of at least about 3 years, and wherein the diet comprises at least one antioxidant selected from the group consisting of vitamin E, vitamin C, α-lipoic acid and/or plant meal, the antioxidant being present in a total antioxidant amount effective to achieve such inhibition. The method of the invention will be found especially beneficial to a dog maintained on the fortified diet for an extended period of at least about 3 years, and preferably for the duration of the dog's life.

In a further aspect, the present invention provides kits suitable for administering one or more antioxidants to an animal. The kits comprise in separate containers in a single package or in separate containers in a virtual package, as appropriate for the kit component, at least one antioxidant and at least one of (1) one or more ingredients suitable for consumption by an animal, (2) instructions for how to combine the antioxidants and other kit components to produce a composition useful for inhibiting a decline in learning and/or memory in animals, and (3) instructions for how to use the antioxidants and other components of the present invention, particularly to inhibit a decline in learning and/or memory in animals. When the kit comprises a virtual package, the kit is limited to instructions in a virtual environment in combination with one or more physical kit components. The kit contains the antioxidants and other components in amounts sufficient to inhibit a decline in learning and/or memory in animals. Typically, the antioxidants and the other suitable kit components are admixed just prior to consumption by an animal. In one embodiment, the kit contains a packet containing one or more one or more antioxidants and a container of food for consumption by an animal. The kit may contain additional items such as a device for mixing the antioxidants and ingredients or a device for containing the admixture, e.g., a food bowl. In another embodiment, the antioxidants are mixed with additional nutritional supplements such as vitamins and minerals that promote good health in an animal.

In another aspect, the present invention provides a means for communicating information about or instructions for one or more of (1) using one or more antioxidants to inhibit a decline in learning and/or memory in animals, (2) admixing one or more antioxidants with the other components of the present invention, (3) administering one or more antioxidants to an animal, alone or in combination with the other elements of the present invention, and (4) using the kits of the present invention for inhibiting a decline in learning and/or memory in animals. The means comprises a document, digital storage media, optical storage media, audio presentation, or visual display containing the information or instructions. Preferably, the communication means is a displayed web site or a brochure, product label, package insert, advertisement, or visual display containing such information or instructions. Useful information includes one or more of (1) methods and techniques for combining and administering the antioxidants and/or other components and (2) contact information for animals or their caregivers to use if they have a question about the invention and its use. Useful instructions include amounts for mixing and administration amounts and frequency. The communication means is useful for instructing on the benefits of using the present invention and communicating the approved methods for administering the invention to an animal.

In a further aspect, the present invention provides for a use of a composition comprising a decline in learning and/or memory amount of at least one antioxidant to prepare a medicament. In another, the invention provides for the use of such composition to prepare a medicament for inhibiting a decline in learning and/or memory in animals. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal. The medicament may further comprise one or more omega-3 fatty acids in amounts sufficient to inhibit a decline in learning and/or memory.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a method" or "a food" includes a plurality of such methods or foods. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

EXAMPLE

The invention can be further illustrated by the following examples of preferred embodiments thereof, although it will be understood that these examples are included merely for purposes of illustration and are not intended to limit the scope of the invention unless otherwise specifically indicated.

Example 1

Seventeen young dogs of age 2-5 years were trained for six months on baseline learning and memory models in a standardized fashion. Group assignment of dogs to either a control food or an antioxidant-fortified food was based upon performance in these baseline models to assure that the dog assignments were balanced with respect to baseline level of cognitive function. The diet and methods of feeding that diet have been substantially described by Milgram et al. (2004) Experimental Gerontology 39(5), 753-765 and Milgram et al. (2005) Neurobiology of Aging 26(1), 77-90. Eight dogs were initially assigned to the control diet group and nine dogs to the antioxidant fortified diet. The antioxidant-fortified diet comprised basal dog food diet fortified with vitamin E, vitamin C, α-lipoic acid and fruit and vegetable meals. Table 1 shows the levels of vitamin E, vitamin C, α-lipoic acid and fruit and vegetable meals in the two diets.

TABLE 1

Comparison of Control Food to Antioxidant Fortified Food

| INGREDIENT | CONTROL FOOD | FORTIFIED FOOD |
|---|---|---|
| Vitamin E | Appx 100 ppm | Appx 1000 ppm |
| l-Carnitine | None added | Appx 260 ppm |
| dl-α-lipoic acid | None added | Appx 120 ppm |
| Vitamin C | None added | Appx 80 ppm |
| Tomato Pomace* | None added | 1% |
| Dried Spinach* | None added | 1% |
| Dried Carrot* | None added | 1% |
| Dried Citrus Pulp* | None added | 1% |
| Dried Grape Pomace* | None added | 1% |

*Vegetables and Fruit Ingredients were added at 1% of the formula in exchange for corn.

The dogs were maintained on the assigned diet for 3 years. After 3 years on the control diet, three of six dogs passed a learning test involving simple shape discrimination while nine of nine dogs on the fortified diet passed the same learning test. The shape discrimination task involved presenting two wooden objects that are identical in thickness texture and color but different in shape. Subjects were given up to 40 training sessions to successfully complete the 2-stage learning criterion where a reward is given for the correct choice. The criterion is set as achieving a score of 8 of 10 correct for two consecutive days followed by a subsequent three days of an average of 70%. Once the initial discrimination is successfully achieved the reward for is reversed. Two dogs on the control diet and none on the fortified diet were dropped from the study for lack of motivation on the testing paradigm.

Table 2 illustrates the results of a memory test, delayed non-match to sample. None of the six dogs on the control diet passed the memory test while four of eight dogs on the antioxidant-fortified diet passed. This study showed that dogs on the antioxidant fortified diet retained memory for longer periods of time than the dogs on the control diet. The delayed non matching task consists of an initial presentation of the sample stimulus over the centre food well. Following a delay, a second presentation occurs with the sample stimulus presented along with a novel, second stimulus (delayed non match to sample or DNMS) At the four-year retest, only one of the animals in the control group was able to achieve criterion level of performance. Maximal memory is operationally defined as the longest delay interval that an animal could satisfactorily complete the two stage criterion as previously defined within 40 test sessions.

TABLE 2

Results of Memory Test

| | Mean maximal memory (seconds) | | |
|---|---|---|---|
| Diet group | Baseline | baseline + 1 year | baseline + 3 years |
| Control | 40 | 10 | 0 |
| Fortified | 58 | 37 | 49 |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for retaining memory as measured by a learning test involving the ability to discriminate simple shapes in an animal about 1 to about 6 years of age comprising maintaining the animal for at least three years on an antioxidant-fortified diet comprising: (a) antioxidants including at least 300 ppm of vitamin E, at least 10 ppm of vitamin C, and at least 25 ppm of α-lipoic acid based on a weight of the diet; and (b) at least one omega-3 fatty acid, wherein the animal is a young adult animal, and wherein the animal is a canine or a feline.

2. The method of claim 1 wherein the animal is the canine and the diet comprises a canned moist dog food or a dry dog food.

3. The method of claim 1 wherein the diet further comprises plant meal.

4. The method of claim 3 wherein the plant meal comprises fruit meal and/or vegetable meal.

5. The method of claim 1 wherein the diet is fortified with a nutritional supplement having the antioxidants as ingredients thereof.

6. The method of claim 1 wherein the antioxidants are distributed substantially homogeneously through a food component of the diet.

7. The method of claim 1 wherein the antioxidants are present in a food component of the diet in whole or in part on surfaces of food pieces.

8. The method of claim 1 further comprising adding to a food component of the diet an antioxidant composition that comprises a powder or liquid carrier having the antioxidant diluted or dispersed therein.

* * * * *